United States Patent [19]

Kadin

[11] Patent Number: 4,690,943

[45] Date of Patent: Sep. 1, 1987

[54] ANALGESIC AND ANTIINFLAMMATORY 1,3-DIACYL-2-OXINDOLE COMPOUNDS

[75] Inventor: Saul B. Kadin, New London, Conn.

[73] Assignee: Pfizer Inc., New York, N.Y.

[21] Appl. No.: 747,194

[22] Filed: Jun. 20, 1985

Related U.S. Application Data

[63] Continuation-in-part of Ser. No. 652,372, Sep. 19, 1984, abandoned.

[51] Int. Cl.$^4$ .................... A61K 31/40; C07D 209/34
[52] U.S. Cl. .................... 514/418; 548/214; 548/236; 548/247; 548/248; 548/336; 548/374; 548/468; 548/486; 548/127; 548/134; 548/136; 548/181; 514/255; 514/256; 514/339; 514/361; 514/362; 514/363; 514/365; 514/372; 514/374; 514/378; 514/397; 514/406; 514/414; 544/333; 544/405; 546/273
[58] Field of Search .................... 548/486; 514/418

[56] References Cited

U.S. PATENT DOCUMENTS

| | | | |
|---|---|---|---|
| 3,189,617 | 6/1965 | Archer et al. | 548/486 |
| 3,462,450 | 8/1969 | Shen | 260/326.12 |
| 3,519,592 | 7/1970 | Holden | 260/240 |
| 3,631,177 | 12/1971 | Holden | 260/325 |
| 3,634,453 | 1/1972 | McManus et al. | 514/962 |
| 3,749,731 | 7/1973 | Zinnes et al. | 260/306.8 |
| 3,856,967 | 12/1974 | Allais et al. | 424/274 |
| 3,975,531 | 8/1976 | Welstead et al. | 424/274 |
| 4,622,336 | 11/1986 | Achini | 548/490 |

FOREIGN PATENT DOCUMENTS

| | | |
|---|---|---|
| 46-14898 | 4/1971 | Japan . |
| 48-14667 | 2/1973 | Japan . |
| 1158532 | 7/1969 | United Kingdom . |
| 1206995 | 9/1970 | United Kingdom . |

OTHER PUBLICATIONS

F. Kosuge et al., Chemical Abstracts 104:5731g (1986), Synthesis and some Reactions of 6-Bromooxindole.
A. Andreani et al., Chemical Abstracts 90:38743r (1979), Synthesis of 3-Dimethylaminomethylidene-2-Indolinones.
Pakula et al., *Chemical Abstracts*, 72:12563(k) (1970).
Brenner et al., *Chemical Abstracts*, 72:12565(n) (1970).
Shen et al., *Chemical Abstracts*, 72:12566(p) (1970).
Wenkert et al., *Journal of the American Chemical Society*, 80, 4899 (1958).
Bunnett et al., *Organic Syntheses*, vol. 40, 1 (1960).
Bruce, *Journal of the Chemical Society* (London), 5302 (1962).
Tacconi et al., *Tetrahedron* 27, 561 (1971).
Kisteneva, *Chemical Abstracts*, 51:5044(a) (1957).

*Primary Examiner*—Mary E. Ceperley
*Attorney, Agent, or Firm*—Peter C. Richardson; Lawrence C. Akers; J. Trevor Lumb

[57] ABSTRACT

Certain novel 2-oxindole compounds, having an acyl substituent at both the 1-position and the 3-position, are inhibitors of the cyclooxygenase (CO) and lipoxygenase (LO) enzymes, and are useful as analgesic agents and antiinflammatory agents in mammalian subjects. These 1,3-diacyl-2-oxindole compounds are of particular value for acute administration for ameliorating pain in human patients recovering from surgery or trauma, and also for chronic administration to human subjects for alleviating the symptoms of chronic diseases such as rheumatoid arthritis and osteoarthritis.

18 Claims, No Drawings

ANALGESIC AND ANTIINFLAMMATORY 1,3-DIACYL-2-OXINDOLE COMPOUNDS

CROSS-REFERENCE TO RELATED APPLICATION

This application is a continuation-in-part of application Ser. No. 652,372, filed Sept. 19, 1984, and now abandoned.

BACKGROUND OF THE INVENTION

This invention relates to new chemical compounds. More particularly, these new chemical compounds are derivatives of 2-oxindole and they are further substituted at the 1- and the 3-position by an acyl group. These new chemical compounds are inhibitors of both the cyclooxygenase (CO) and lipoxygenase (LO) enzymes.

The compounds of this invention possess analgesic activity in mammals, particularly man, and they are useful therefore for acute administration for ameliorating or eliminating pain, such as the pain experienced by patients recovering from surgery or trauma.

In addition to their usefulness for acute administration to combat pain, the compounds of this invention are useful for chronic administration to mammals, particularly man, to alleviate the symptoms of chronic diseases, such as the inflammation and pain associated with rheumatoid arthritis and osteoarthritis.

SUMMARY OF THE INVENTION

This invention provides novel 1,3-diacyl-2-oxindole compounds of the formula

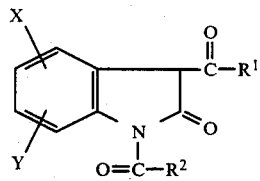

and the pharmaceutically-acceptable base salts thereof, wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

$R^1$ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)alkyl having 1 to 3 carbons in said alkyl, naphthyl and $-(CH_2)_n-Q-R^\circ$;

wherein the substituent on said substituted phenyl, said (substituted phenyl)alkyl and said (substituted phenoxy)alkyl is selected from the group consisting of fluoro, chloro, bromo, alkyl having 1 to 4 carbons, alkoxy having 1 to 4 carbons and trifluoromethyl; n is zero, 1 or 2; Q is a divalent radical derived from a compound selected from the group consisting of furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine and pyrazine; and $R^\circ$ is hydrogen or alkyl having 1 to 3 carbons;

and $R^2$ is alkyl having from 1 to 5 carbons.

Said compounds of formula I are active as analgesic agents, and as agents for treating inflammatory diseases, such as the arthritides. Accordingly, this invention also provides a method of eliciting an analgesic response in a mammalian subject, especially man; a method of treating an inflammatory disease in a mammalian subject, especially man; and pharmaceutical compositions comprising a compound of formula I and a pharmaceutically-acceptable carrier.

A preferred group of compounds of this invention consists of the compounds of formula I, wherein X and Y are each hydrogen and $R^1$ is selected from the group consisting of 2-furyl, 2-thienyl, 3-pyridyl and (2-thienyl)methyl.

A further preferred group of compounds of this invention consists of the compounds of formula I, wherein X is 5-chloro, Y is hydrogen and $R^1$ is selected from the group consisting of 2-furyl, 2-thienyl, 3-pyridyl and (2-thienyl)methyl.

Especially preferred individual compounds of the invention are:
1-acetyl-3-(2-thenoyl)-2-oxindole,
1-acetyl-3-([2-thienyl]acetyl)-2-oxindole, and
5-chloro-1-acetyl-3-(2-thenoyl)-2-oxindole.

Useful as intermediates to the analgesic and antiinflammatory compounds of the formula I are the 1-acyl-2-oxindole compounds of the formula

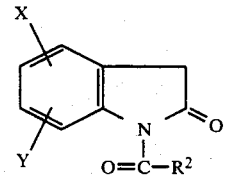

wherein X, Y and $R^2$ are as defined previously. A preferred sub-group of compounds of the formula II consists of those compounds in which X is hydrogen, 5-fluoro, 5-chloro or 5-trifluoromethyl; Y is hydrogen, 6-fluoro, 6-chloro or 6-trifluoromethyl; and $R^2$ is alkyl having 1 to 5 carbons; provided that X and Y are not both hydrogen. The compounds of formula II in said latter preferred sub-group are novel, and as such they form part of this invention.

DETAILED DESCRIPTION OF THE INVENTION

This invention relates to the compounds of formula I, and these compounds are named as derivatives of 2-oxindole, the compound of the structure:

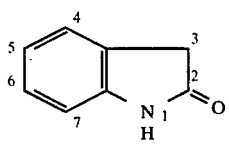

Additionally, as will be appreciated by one skilled in the art, the analgesic and anti-inflammatory compounds of this invention of formula I, wherein X, Y, $R^1$ and $R^2$ are defined previously, are capable of enolization, and therefore they can exist in one or more tautomeric (enolic) forms. All such tautomeric (enolic) forms of the compounds of formula I are considered to be within the scope of this invention.

The compounds of the formula I are prepared from the appropriate 2-oxindole compound of the formula III:

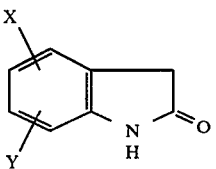

wherein X and Y are as defined previously, by attaching the substituent $'C(=O)-R^2$ to the 1—position and the $-C(=O)-R^1$ substituent to the 3—position. These substituents can be attached in either order, and this leads to two variations in the method for making the compounds of formula I. These are shown in Scheme A. However, the preferred method of preparing the compounds of formula I involves the sequence: compound III to compound IV to I.

SCHEME A

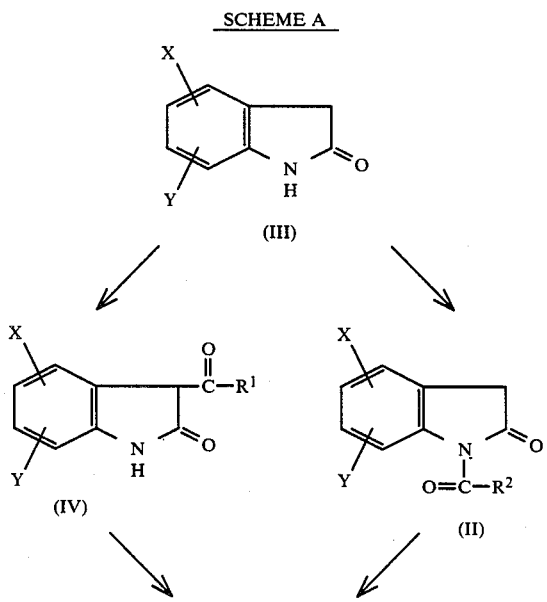

-continued
SCHEME A

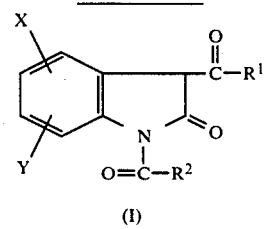

The $-C(=O)-R^2$ substituent can be attached to a compound of the formula IV by reaction with one molar equivalent, or a small excess, of an activated derivative of a carboxylic acid of the formula $R^2-C(=O)OH$, in the presence of from one to four equivalents of a basic agent in an inert solvent. An inert solvent is one which will dissolve at least one of the reactants, and will not adversely interact with either of the reactants or the product. However, in practice a polar, aprotic solvent, such as N,N-dimethylformamide, N,N-dimethylacetamide, N-methylpyrrolidone or dimethyl sulfoxide, is commonly used. Conventional methods for activating the acid of formula $R^2-C(=O)OH$ are used. For example, acid halides, e.g., acid chlorides; symmetrical acid anhydrides, $R^2-C(=O)-O-C(=O)-R^2$; mixed acid anhydrides with a hindered low-molecular weight carboxylic acid, $R^2-C(=O)-O-C(=O)-R^3$, where $R^3$ is a bulky lower-alkyl group such as t-butyl; and mixed carboxylic-carbonic anhydrides, $R^2-C(=O)-O-C(=O)-OR^4$, wherein $R^4$ is a lower alkyl group, can all be used. In addition, N-hydroxyimide esters (such as N-hydroxysuccinimide and N-hydroxyphthalimide esters), 4-nitrophenyl esters, thiol esters (such as thiol phenyl esters) and 2,4,5-trichlorophenyl esters, and the like, can be used.

A wide variety of basic agents can be used in the reaction between a compound of formula IV and the activated derivative of the acid of the formula $R^2-C(=O)OH$. However, preferred basic agents are tertiary amines, such as trimethylamine, triethylamine, tributylamine, N-methylmorpholine, N-methylpiperidine and 4-(N,N-dimethylamino)pyridine.

The reaction between a compound of the formula IV and the activated derivative of the acid of formula $R^2-C(=O)-OH$ is usually carried out in the temperature range from $-20°$ to $25°$ C. In general, temperatures at the lower end of this range are used when highly activated derivatives of an acid of formula $R^2-C(=O)-OH$ are used, while higher temperatures are used when only mildly activated derivatives of the acid $R^2-C(=O)-OH$ are used. In most instances, the reaction proceeds quite quickly, and reaction times of from 30 minutes to a few hours are common. At the end of the reaction, the reaction medium is usually diluted with water and acidified, and then the product of formula I can be recovered by filtration. It can be purified by standard methods, such as recrystallization.

The $-C(=O)-R^1$ side-chain can be attached to a compound of the formula II by reaction with one molar equivalent, or a small excess, of an activated derivative of a carboxylic acid of the formula $R^1-C(=O)-OH$. This acylation reaction is carried out in the same manner as that described for reaction of a compound of the formula IV with an activated derivative of a carboxylic acid of the formula $R^2-C(=O)-OH$.

The —C(=O)—R¹ side-chain can be attached to a compound of the formula III by reaction with a derivative of the appropriate acid of the formula R¹—C(=O)—OH, in a lower-alkanol solvent (e.g. ethanol), in the presence of an alkali metal salt of the lower-alkanol solvent (e.g. sodium ethoxide), according to standard procedures. Typical derivatives of the acid of the formula R¹—C(=O)OH which can be used include acid chlorides, acid anhydrides of the formula R¹—C(=O)—O—C(=O)—R¹, R¹—C(=O)—O—C(=O)—R³ and R¹—C(=O)—O—C(=O)—OR⁴, and simple alkyl esters of the formula R¹—C(=O)—OR⁴; wherein R³ and R⁴ are as defined previously. Usually, a small excess of the derivative of the acid of formula R¹—C(=O)—OH is used, and the alkoxide salt is usually present in an amount from one to two molar equivalents, based on said derivative of the acid of formula R¹—C(=O)OH. The reaction between the derivative of the acid of the formula R¹—C(=O)OH and the compound of formula III is usually started at 0° to 25° C., but it is then usual to heat the reaction mixture at a temperature in the range from 50° to 130° C., and preferably at about 80° C., to complete the reaction. Under these circumstances, reaction times of a few hours, e.g. two hours, up to a few days, e.g., two days, are commonly used. The reaction mixture is then cooled, diluted with an excess of water, and acidified. The product of formula IV can then be recovered by filtration or by the standard procedure of solvent extraction.

The —C(=O)—R² side-chain can be attached to a compound of the formula III by reaction with the appropriate acid anhydride of the formula [R²—C(=O)]₂O. Usually the compound of formula III is reacted with from one to three equivalents, and preferably 1.2 to 1.5 equivalents, of the anhydride in the absence of solvent, at a temperature in the range from 80° to 130° C., and preferably about 100° C., for several hours (e.g., about 4 hours). If desired, however, an inert solvent such as toluene can be used. At the end of the reaction, the product of formula II can be recovered by removal of the excess anhydride and any solvent by evaporation. The crude product is usually pure enough for conversion into a compound of formula I. The 2-oxindole compounds of formula III are prepared by known methods, or methods analogous to known methods. Consult: "Rodd's Chemistry of Carbon Compounds," Second Edition, S. Coffey editor, Volume IV Part A, Elsevier Scientific Publishing Company, 1973, pp. 448–450; Gassman et al., *Journal of Organic Chemistry*, 42, 1340 (1977); Wright et al., *Journal of the American Chemical Society*, 78, 221 (1956); Beckett et al., *Tetrahedron*, 24, 6093 (1968); U.S. Pat. Nos. 3,882,236, 4,006,161 and 4,160,032; Walker, *Journal of the American Chemical Society*, 77, 3844 (1955); Protiva et al., *Collection of Czechoslovakian Chemical Communications*, 44, 2108 (1979); McEvoy et al., *Journal of Organic Chemistry*, 38, 3350 (1973); Simet, *Journal of Organic Chemistry*, 28, 3580 (1963); Wieland et al., *Chemische Berichte*, 96, 253 (1963); and references cited therein.

The compounds of the formula I are acidic and they form base salts. All such base salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. Typical salts of the compounds of formula I which can be prepared are primary, secondary and tertiary amine salt, alkali metal salts and alkaline earth metal salts. Especially valuable are the ethanolamine, diethanolamine and triethanolamine salts.

Basic agents suitably employed in salt formation belong to both the organic and inorganic types, and they include organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are primary amines, such as n-propylamine, n-butylamine, aniline, cyclohexylamine, benzylamine, p-toluidine, ethanolamine and glucamine; secondary amines, such as diethylamine, diethanolamine, N-methylglucamine, N-methylaniline, morpholine, pyrrolidine and piperidine; tertiary amines, such as triethylamine, triethanolamine, N,N-dimethylaniline, N-ethylpiperidine and N-methylmorpholine; hydroxides, such as sodium hydroxide; alkoxides, such as sodium ethoxide and potassium methoxide; hydrides, such as calcium hydride and sodium hydride; and carbonates, such as potassium carbonate and sodium carbonate.

The compounds of formula I possess analgesic activity. This activity has been demonstrated in mice by showing blockade of the abdominal stretching induced by administration of 2-phenyl-1,4-benzoquinone (PBQ), using a method based on that of Siegmund et al., *Proc. Soc. Exp. Biol. Med.*, 95, 729–731, (1957), as adapted for high throughput (see further Milne and Twomey, *Agents and Actions*, 10, 31–37, [1980]). The mice used in these experiments were Carworth males, albino CF-1 strain, weighing 18–20 g. All mice were fasted overnight prior to drug administration and testing.

The compounds of formula I were dissolved or suspended in a vehicle consisting of ethanol (5%), emulphor 620 (a mixture of polyoxyethylene fatty acid esters, 5%) and saline (90%). This vehicle also served as control. Doses were on a logarithmic scale (i.e., ... 0.32, 1.0, 3.2, 10, 32 ... mg/kg). The route of administration was oral, with concentrations varied to allow a constant dosage volume of 10 ml/kg of body weight. The aforesaid method of Milne and Twomey was used to determine efficacy and potency. Mice were treated with compounds orally, and one hour later received PBQ, 2 mg/kg, intraperitoneally. Individual mice were then immediately placed in a warmed Lucite (transparent plastic) chamber, and, starting five minutes after PBQ administration, the number of abdominal constrictions during the subsequent 5 minutes was recorded. The degree of analgesic protection (% MPE) was calculated on the basis of suppression of abdominal constriction relative to counts from response data for generation of an MPE₅₀, the best estimate of the dose that reduces abdominal constriction to 50% of control levels.

The compounds of formula I also possess anti-inflammatory activity. This activity has been demonstrated in rats by a method based on the standard carrageenin-induced rat-foot edema test. (Winter et al., *Proc. Soc. Exp. Biol. Med.*, 111, 544, [1963]).

Unanesthetized, adult, male, albino rats of 150 g to 190 g body weight were numbered, weighed, and an ink mark placed on the right lateral malleolus. Each paw was immersed in mercury exactly to the ink mark. The mercury was contained in a glass cylinder, connected to a Statham Pressure Transducer. The output from the transducer was fed through a control unit to a microvoltameter. The volume of mercury displaced by the immersed paw was read. Drugs were given by gavage. One hour after drug administration, edema was induced by injection of 0.05 ml of 1% solution of carrageenin into the plantar tissue of the marked paws. Immediately thereafter, the volume of the injected foot was measured. The increase in foot volume 3 hours after the injection of carrageenin constitutes the individual inflammatory response.

The analgesic activity of the compounds of formula I makes them useful for acute administration to mammals for the control of pain, e.g., post-operative pain and the pain of trauma. Additionally the compounds of formula I are useful for chronic administration to mammals for the alleviation of the symptoms of chronic diseases, such as the inflammation of rheumatoid arthritis, and the pain associated with osteoarthritis and other musculoskeletal disorders.

When a compound of the formula I or a pharmaceutically acceptable salt thereof is to be used as either an analgesic agent or an anti-inflammatory agent, it can be administered to a mammalian subject either alone, or, preferably, in combination with pharmaceutically-acceptable carriers or diluents in a pharmaceutical composition, according to standard pharmaceutical practice. A compound can be administered orally or parenterally. Parenteral administration includes intravenous, intramuscular, intraperitoneal, subcutaneous and topical administration.

In a pharmaceutical composition comprising a compound of formula I, or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

For oral use of a compound of formula I of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifiying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a compound of formula I or salt thereof is used in a human subject, the daily dosage will normally be determined by the prescribing physician. Moreover, the dosage will vary according to the age, weight and response of the individual patient, as well as the severity of the patient's symptoms and the potency of the particular compound being administered. However, for acute administration to relieve pain, an effective analgesic response eliciting dose in most instances will be 0.1 to 1.0 g as needed (e.g., every four to six hours). For chronic administration to alleviate (treat) inflammation and pain, in most instances an effective dose will be from 0.1 to 1.5 g per day, and preferably 0.3 to 1.0 g per day, in single or divided doses. On the other hand, it may be necessary to use dosages outside these limits in some cases.

The following examples and preparations are being provided solely for the purpose of further illustration.

EXAMPLE 1

1-Acetyl-3-(2-thenoyl)-2-oxindole

To a stirred solution of 486 mg (2.0 mmole) of 3-(2-thenoyl)-2-oxindole in 4 ml of N,N-dimethylformamide was added 538 mg (4.4 mmole) of 4-(N,N-dimethylamino)pyridine. The resulting mixture was cooled in an ice-bath, and then a solution of 225 mg (2.2 mmole) of acetic anhydride in 2 ml of N,N-dimethylformamide was added dropwise, with stirring during about 1 minute. The cooling bath was removed and stirring was continued for 1 hour, and then the reaction mixture was poured onto a mixture of 50 ml of water and 1.7 ml of 3N hydrochloric acid. The resulting mixture was cooled in an ice-bath, and the solid was recovered by filtration. This afforded 528 mg of a yellow solid. The yellow solid was recrystallized from ca. 15 ml of ethanol, giving 300 mg of the title compound as yellow crystals, m.p. 139°–140° C.

Analysis: Calcd. for $C_{15}H_{11}NO_3S$: C, 63.14; H, 3.89; N, 4.91%. Found: C, 63.15; H, 3.90; N, 4.87%.

EXAMPLE 2

1-Acetyl-3-(2-furoyl)-2-oxindole

Acetylation of 3-(2-furoyl)-2-oxindole with acetic anhydride, substantially according to the procedure of Example 1, afforded a 73% yield of the title compound, m.p. 137.5°–138.5° C.

Analysis: Calcd. for $C_{15}H_{11}NO_4$: C, 66.91; H, 4.12; N, 5.20%. Found: C, 66.93; H, 4.23; N, 5.12%.

EXAMPLE 3

1-Acetyl-3-(3-pyridylcarbonyl)-2-oxindole

Acetylation of 3-(3-pyridylcarbonyl)-2-oxindole with acetic anhydride, substantially according to the procedure of Example 1, afforded a 53% yield of the title compound, m.p. 141°–142.5° C.

EXAMPLE 4

Acylation of the appropriate 3-acyl-2-oxindole with the requisite acid anhydride of the formula $(R^2CO)_2O$, substantially according to the procedure of Example 1, afforded the following compounds:

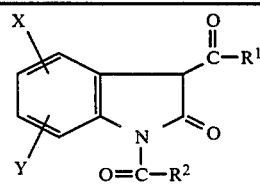

| X | Y | $R^1$ | $R^2$ | Melting Point (°C.) |
|---|---|---|---|---|
| 5-Cl | H | 2-thienyl | methyl | 167–169 |
| 5-Cl | H | 2-furyl | methyl | 174–175 |
| 5-Cl | H | phenyl | methyl | 164–167 |
| 5-Cl | H | benzyl | methyl | 167–168 |
| 5-Cl | H | (2-thienyl)methyl | methyl | 170–171.5 |

-continued

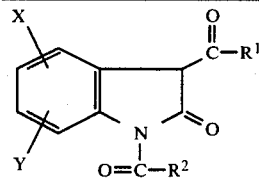

| X | Y | R¹ | R² | Melting Point (°C.) |
|---|---|---|---|---|
| 5-F | H | 2-furyl | methyl | 161–163 |
| H | H | 2-thienyl | neopentyl | 142–145 |
| 5-Cl | H | 2-thienyl | neopentyl | 142–143.5 |
| 5-F | H | 2-thienyl | neopentyl | 152–153 |
| H | H | (2-thienyl)methyl | neopentyl | 120–122 |
| 5-Cl | H | benzyl | neopentyl | 128–130 |
| H | H | benzyl | isopropyl | 125–128 |
| H | H | 2-furyl | isopropyl | 112–115 |
| 5-Cl | H | 2-furyl | neopentyl | 131–132 |
| 5-Cl | H | 2-thienyl | isopropyl | 150–151 |
| 5-F | H | 2-furyl | isopropyl | 114–116 |
| 5-NO₂ | H | 2-furyl | isopropyl | 183–185 |
| H | H | 2-thienyl | isopropyl | 173–175 |
| 5-F | H | 2-thienyl | isopropyl | 147–149 |
| 5-Cl | H | (2-thienyl)methyl | neopentyl | 139–140.5 |
| 5-Cl | H | benzyl | isopropyl | 145–146.5 |
| 5-Cl | H | 2-thienyl | ethyl | 180–183 |
| H | H | (2-thienyl)methyl | isopropyl | 107–109 |
| H | H | 2-furyl | neopentyl | 123–125 |
| 5-Cl | H | 2-furyl | ethyl | 195–196.5 |
| 5-F | H | 2-furyl | ethyl | 153–154.5 |
| 5-F | 6-Cl | 2-thienyl | methyl | 183–185 |
| 5-F | 6-F | 2-thienyl | methyl | 166–168 |

EXAMPLE 5

By acylation of the appropriate 3-acyl-2-oxindole compound with acetic anhydride, using the procedure of Example 1, the following compounds can be prepared.

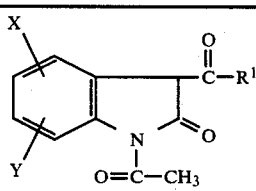

| X | Y | R¹ |
|---|---|---|
| H | H | 3-furyl |
| H | H | isobutyl |
| H | H | cycloheptyl |
| H | H | 3-phenylpropyl |
| H | H | 3-pyrrolyl |
| H | H | phenyl |
| 5-F | H | 2-furyl |
| 5-F | H | cyclopentyl |
| 5-F | H | 3-furyl |
| 6-F | H | (3-thienyl)methyl |
| 6-F | H | (2-furyl)methyl |
| 5-Cl | H | (2-thienyl)methyl |
| 6-Cl | H | 2-furyl |
| 5-Br | H | (3-furyl)methyl |
| 6-Br | H | n-hexyl |
| 5-CF₃ | H | n-butyl |
| 6-CF₃ | H | 3-thienyl |
| 6-CF₃ | H | cyclopropyl |
| 6-CF₃ | H | ethyl |
| 6-CF₃ | H | 1-phenylethyl |
| 5-n-OC₄H₉ | H | 2-furyl |
| 5-OC₂H₅ | H | 2-thienyl |
| 7-Cl | H | (2-thienyl)methyl |
| 5-Cl | H | 2-fluorophenyl |
| 5-n-C₄H₉ | H | 2-furyl |

-continued

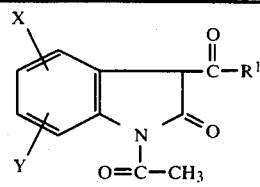

| X | Y | R¹ |
|---|---|---|
| 5-CH₃ | H | 4-bromophenyl |
| 6-SCH₃ | H | 3-n-butylphenyl |
| 5-CF₃ | H | 3-methoxyphenyl |
| 5-n-SC₄H₉ | H | 4-isobutoxyphenyl |
| 5-CH₃ | 6-CH₃ | 3-(phenyl)propyl |
| 6-OCH₃ | H | 3-(phenoxy)propyl |
| 6-SCH₃ | H | 2-thienyl |
| 5-NO₂ | H | (3-fluorophenoxy)methyl |
| 5-C₃H₅¹ | H | 2-thienyl |
| 5-C₇H₁₃² | H | 2-furyl |
| 5-Cl | H | methyl |
| H | H | cyclobut-1-en-1-yl |
| 5-Cl | H | cyclohept-1-en-1-yl |
| 6-F | H | (thiophenoxy)methyl |
| 5-CF₃ | H | 3-(thiophenoxy)propyl |
| H | H | 1-imidazolyl |
| 5-Cl | 6-Cl | 2-tetrahydropyranyl |
| 6-n-SC₄H₉ | H | (4-chlorophenoxy)methyl |
| 5-OCH₃ | 6-OCH₃ | (2-thienyl)methyl |
| 5-F | 6-Cl | (4-bromophenoxy)methyl |
| 5-F | 6-Cl | 2-tetrahydrothiopyranyl |
| 6-Cl | H | (2-methylphenoxy)methyl |
| 6-Br | H | (4-isobutylphenoxy)methyl |
| 6-n-SC₄H₉ | H | 2-thienyl |
| 7-Cl | H | (3-methoxyphenoxy)methyl |
| 4-SCH₃ | H | (4-butoxyphenoxy)methyl |
| H | 6-SCH₃ | 3-furyl |
| 4-CH₃ | 5-CH₃ | 3-thienyl |
| 6-SCH₃ | H | 3-methyl-2-furyl |
| H | 5-CF₃ | 5-propyl-2-furyl |
| 5-CH(CH₃)₂ | H | 3-methyl-2-thienyl |
| 5-F | 6-Cl | 5-propyl-2-thienyl |
| 5-NO₂ | H | 3-(3-thienyl)propyl |
| 5-OC₂H₅ | H | 1-(2-furyl)ethyl |
| 7-Cl | H | 3-(2-furyl)propyl |
| 6-CH₃SO | H | 2-thienyl |
| 6-n-C₄H₉SO | H | 2-furyl |
| 4-CH₃SO₂ | H | 2-fluorophenyl |
| 6-n-C₄H₉SO₂ | H | 2-thiazolyl |
| 5-NO₂ | H | 2-(3-thienyl)ethyl |
| 6-C₆H₅ | H | 4-chlorophenyl |
| H | 5-Br | 2-(2-tolyl)ethyl |
| 5-CH₃CO | H | 4-trifluoromethylphenyl |
| 6-n-C₃H₇CO | H | 4-isothiazolyl |
| 5-Cl | H | 1-naphthyl |
| 5-C₆H₅CO | H | 1,2,3-thiadiazol-4-yl |
| 5-C₄H₃SCO³ | H | 3-(3-chlorophenyl)propyl |
| 6-CF₃ | H | (4-thiazolyl)methyl |
| 6-F | H | 1,2,5-thiadiazol-3-yl |
| 5-CH₃CONH | H | 1-methyl-1-phenylethyl |
| 5-Cl | 6-Cl | 5-methyl-4-isoxazolyl |
| 5-(CH₃)₂CH—CONH | H | 2-(4-isopropyl-phenyl)ethyl |
| 5-C₆H₅CONH | H | 2-thienyl |
| 5-CH₃ | 6-CH₃ | 4-isopropoxyphenyl |
| 5-SO₂N(CH₃)₂ | H | 3-pyrazolyl |
| 5-F | 6-F | 4-chlorophenoxy |
| 5-SO₂N(n-C₃H₇)₂ | H | 2-tetrahydrofuryl |
| H | 4-Cl | 4-pyridyl |
| 6-Cl | H | 3-tetrahydrothienyl |
| H | H | 5-pyrimidyl |
| 5-CH₃ | 6-F | 2-pyrazinyl |
| H | H | 2-n-propyl-4-thiazolyl |
| 5-Br | H | 2-oxazolyl |
| H | H | 3-isoxazolyl |
| H | H | 1,3,4-thiadiazol-2-yl |

¹cyclopropyl
²cycloheptyl
³5-(2-thenoyl)

EXAMPLE 6

The procedure of Example 1 is repeated, except that the 3-(2-thenoyl)-2-oxindole is replaced by an equimolar amount of:
3-([2-thienyl]acetyl)-2-oxindole,
5-fluoro-3-cyclopentylcarbonyl-2-oxindole,
5-chloro-3-([2-thienyl]acetyl)-2-oxindole,
6-chloro-3-(2-furoyl)-2-oxindole,
6-bromo-3-n-hexyl-2-oxindole and
6-trifluoromethyl-3-(3-phenylpropionyl)-2-oxindole,
respectively, and the acetic anhydride is replaced by an equimolar amount of:
propionic anhydride,
caproyl chloride,
butyric anhydride,
propionic anhydride,
isovaleric anhydride and
isocaproyl chloride,
respectively. This affords the following compounds:
N-propionyl-3-([2-thienyl]acetyl)-2-oxindole,
N-caproyl-5-fluoro-3-cyclopentylcarbonyl-2-oxindole,
N-butyroyl-5-chloro-3-([2-thienyl]acetyl)-2-oxindole,
N-propionyl-6-chloro-3-(2-furoyl)-2-oxindole,
N-isovaleroyl-6-bromo-3-n-hexyl-2-oxindole and
N-isocaproyl-6-trifluoromethyl-3-(3-phenylpropionyl)-2-oxindole,
respectively.

EXAMPLE 7

1-Acetyl-3-([2-thienyl]acetyl)-2-oxindole

A stirred mixture of 1.29 g (5.0 mmole) of 3-([2-thienyl]acetyl)-2-oxindole, 1.22 g (10.0 mmole) of 4-(N,N-dimethylamino)pyridine and 15 ml of N,N-dimethylformamide was cooled in an ice-bath, and then 562 mg (5.5 mmole) of acetic anhydride was added dropwise, with stirring, during 1 minute. Stirring was continued for 3.25 hours at ice-bath temperature, and then the reaction mixture was filtered. The filtrate was poured onto a mixture of 3N hydrochloric acid and water, which caused formation of a solid and a gum. The solid was recovered by filtration and the gum was recovered by decantation. The gum was triturated under isopropanol-water giving further solid material, which was also recovered by filtration. The two solids were combined and extracted with hot benzene, leaving a dark, gummy residue. The benzene solution was cooled and evaporated in vacuo, and the residue was recrystallized from toluene to give 66 mg of the title compound, m.p. 136°–137° C. The mother liquors from the recrystallization were evaporated in vacuo and the latter residue was recrystallized from hexane to give a second crop, 90 mg, of the title compound, m.p. 135°–136° C. The second crop was submitted to elemental analysis.

Analysis: Calcd. for $C_{16}H_{13}NO_3S$: C, 64.20; H, 4.38; N, 4.68%. Found: C, 64.36; H, 4.44; N, 4.68%.

EXAMPLE 8

1-Acetyl-3-(2-phenylacetyl)-2-oxindole 3-(2-Phenylacetyl)-2-oxindole was acetylated with acetic anhydride using the procedure of Example 7. When the reaction mixture was poured into a mixture of 3N hydrochloric acid and water, a solid formed. The solid was recovered by filtration and recrystallized from isopropanol to give a 40% yield of the title compound, m.p. 149°–151° C.

The ultraviolet spectrum of the product in methanol showed absorption maxima at 238, 260 and 290 millimicrons. After the addition of 1 drop of KOH, the absorption maxima appeared at 238, 260 and 307 millimicrons.

Analysis: Calcd. for $C_{18}H_{15}NO_3$: C, 73.71; H, 5.15; N, 4.77%. Found: C, 73.23; H, 5.18; N, 4.62%.

EXAMPLE 9

1-Acetyl-3-(3-pyridylcarbonyl)-2-oxindole

A mixture of 476 mg (2.0 mmole) of 3-(3-pyridylcarbonyl)-2-oxindole and 4 ml of acetic anhydride was heated under reflux for 30 minutes The reaction mixture was cooled to room temperature, the bulk of the acetic anhydride was removed by evaporation in vacuo and the residue was triturated under 15 ml of water. The solid was recovered by filtration, dried and triturated under isopropanol. The residue (158 mg) was recrystallized from acetonitrile giving 64 mg of the title compound as red-orange crystals, m.p. 142.5°–143.5° C. A second crop of title compound (40 mg) was obtained from the mother liquors from the recrystallization. The two crops were the same by thin-layer chromatography. The first crop was subjected to elemental analysis.

Analysis: Calcd. for $C_{16}H_{12}N_2O_3$: C, 68.56; H, 4.32; N, 10.00%. Found: C, 68.26; H, 4.38; N, 9.87%.

EXAMPLE 10

Ethanolamine Salt of 1-Acetyl-3-(2-thenoyl)-2-oxindole

To a slurry of 2.85 g of N-acetyl-3-(2-thenoyl)-2-oxindole in 40 ml of methanol is added 610 mg of ethanolamine. The resulting mixture is heated to boiling for 5 minutes, and then it is allowed to cool. The solvent is removed by evaporation in vacuo to give the title salt.

EXAMPLE 11

5-Chloro-1-acetyl-3-(2-thenoyl)-2-oxindole

To a stirred solution of 0.75 g (3.6 mmole) of 5-chloro-1-acetyl-2-oxindole and 0.96 ml (7.9 mmole) of 4-(N,N-dimethylamino)pyridine in 20 ml of N,N-dimethylformamide, cooled to ca. 0° C., was added a solution of 0.4 ml (3.7 mmole) of 2-thenoyl chloride in 5 ml of N,N-dimethylformamide, dropwise, during a few minutes. The reaction mixture was stirred for 30 minutes at ca. 0° C. and then for 3.5 hours at room temperature, and then it was poured into 500 ml of ice-cold 2N hydrochloric acid. The resulting solution was extracted with ethyl acetate, and the extracts were washed with water, followed by saturated sodium chloride solution, and then they were dried using magnesium sulfate. Evaporation of the dried ethyl acetate solution gave 1.1 g of crude product. The latter was purified by column chromatography using silica gel and eluting with dichloromethane-ethyl acetate mixtures, followed by recrystallization from a small volume of toluene, to give 250 mg of the title compound, m.p. 168°–170° C.

The above product was shown to be the same compound as that obtained by reaction of acetic anhydride with 5-chloro-3-(2-thenoyl)-2-oxindole.

Analysis: Calcd. for $C_{15}H_{10}ClNO_3S$: C, 56.34; H, 3.15; N, 4.38% Found: C, 56.40; H, 3.21; N, 4.32%.

EXAMPLE 12

5-Chloro-1-acetyl-2-oxindole

A mixture of 7.0 g (42 mmole) of 5-chloro-2-oxindole and 5.9 ml (63 mmole) of acetic anhydride was heated under nitrogen at reflux for 3.5 hours. The cooled reaction mixture was diluted with 300 ml of ethyl acetate, and the resulting solution was washed with aqueous sodium bicarbonate followed by saturated, aqueous sodium chloride solution. The ethyl acetate solution was then dried ($Na_2SO_4$) and evaporated in vacuo to give 8.3 g of a purple solid. The latter solid was purified by chromatography on silica gel, eluting with 2.5% ethyl acetate in dichloromethane, to give 6.0 g of crude title compound as a yellow solid. The latter solid was recrystallized from ca. 50 ml of ethanol to give 4.7 g of the title compound as pale yellow needles, m.p. 129°–130° C.

EXAMPLE 13

Reaction of the appropriate 2-oxindole with the requisite acid anhydride, substantially according to the procedure of Example 12, afforded the following compounds:
1-acetyl-2-oxindole, m.p. 127°–129° C.;
5-chloro-1-isobutyryl-2-oxindole, m.p. 91°–93° C.; and
6-chloro-5-fluoro-1-acetyl-2-oxindole, m.p. 146°–148° C.

EXAMPLE 14

By reaction of the appropriate 2-oxindole with the necessary acid anhydride, using the procedure of Example 12, the following compounds can be prepared.

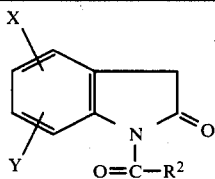

| X | Y | $R^2$ |
|---|---|---|
| 5-$CF_3$ | H | methyl |
| 5-F | H | ethyl |
| 6-Cl | H | ethyl |
| 6-$CF_3$ | H | methyl |
| 5-Cl | 6-Cl | n-pentyl |
| 5-F | 6-F | methyl |

PREPARATION 1

3-(2-Furoyl)-2-oxindole

To a stirred solution of 5.5 g (0.24 mole) of sodium in 150 ml of ethanol was added 13.3 g (0.10 mole) of 2-oxindole at room temperature. The resulting slurry was cooled to ice-bath temperature, and then 15.7 g (0.12 mole) of 2-furoyl chloride was added, dropwise, during 10–15 minutes. The ice-bath was removed, and an additional 100 ml of ethanol was added and then the reaction mixture was heated under reflux for 7 hours. The reaction mixture was allowed to stand overnight and then the solid was filtered off. The solid was added to 400 ml of water and the resulting mixture was acidified using concentrated hydrochloric acid. The mixture was cooled with ice and the solid was collected by filtration. The solid residue was recrystallized from 150 ml of acetic acid, affording 8.3 g of yellow crystals, m.p. 209°–210° C. (dec.).

Analysis: Calcd. for $C_{13}H_9O_3N$: C, 68.72; H, 3.99; N, 6.17%. Found: C, 68.25; H, 4.05; N, 6.20%.

PREPARATION 2

Reaction of 2-oxindole with the appropriate acid chloride using the method of Preparation 1, gave the following additional products:
3-(2-thenoyl)-2-oxindole, m.p. 189°–190° C., 17% yield;
3-(2-[2-thienyl]acetyl)-2-oxindole, m.p. 191°–192.5° C., 38% yield;
3-(2-phenoxyacetyl)-2-oxindole, m.p. 135°–136° C., 42% yield; and
5-chloro-3-(2-[2-thienyl]acetyl)-2-oxindole, m.p. 228°–230° C., 22% yield.

PREPARATION 3

3-(3-Furoyl)-2-oxindole

To a stirred solution of 2.8 g (0.12 mole) of sodium in 200 ml of ethanol was added 13.3 g (0.10 mole) of 2-oxindole, followed by 16.8 g of ethyl 3-furoate. The mixture was heated under reflux for 47 hours, cooled and then the solvent was removed by evaporation in vacuo. The residue was triturated under 200 ml of ether, and the solid was collected by filtration and discarded. The filtrate was evaporated in vacuo, and the residue triturated under isopropyl alcohol and recovered by filtration. The solid was suspended in 250 ml of water, which was then acidified with concentrated hydrochloric acid. This mixture was stirred to give a solid, which was recovered by filtration. This latter solid was recrystallized from acetic acid followed by acetonitrile to give 705 mg of the title compound, m.p. 185°–186° C.

Analysis: Calcd. for $C_{13}H_9O_3N$: C, 68.72; H, 3.99; N, 6.17%. Found: C, 68.72; H, 4.14; N, 6.14%.

PREPARATION 4

Reaction of the appropriate 2-oxindole with the ethyl ester of the requisite carboxylic acid, substantially according to the procedure of Preparation 3 gave the following compounds:
5-chloro-3-(2-thenoyl)-2-oxindole, m.p. 190.5°–192° C., 36% yield;
5-chloro-3-(2-furoyl)-2-oxindole, m.p. 234°–235° C., 54% yield;
5-chloro-3-(2-phenylacetyl)-2-oxindole, m.p. 241°–243° C., 61% yield;
5-fluoro-3-(2-furoyl)-2-oxindole, m.p. 222°–224° C., 51% yield;
5-fluoro-3-(2-thenoyl)-2-oxindole, m.p. 200°–203° C., 26% yield;
6-fluoro-3-(2-furoyl)-2-oxindole, m.p. 239°–242° C., 26% yield; and
6-chloro-5-fluoro-3-(2-thenoyl)-2-oxindole, m.p. 212°–215° C., 20% yield.

In like manner, using the requisite 2-oxindole and ethyl ester, and following substantially the method of Preparation 3, the following compounds can be prepared:
5-trifluoromethyl-3-(2-furoyl)-2-oxindole; and
6-trifluoromethyl-3-(3-thenoyl)-2-oxindole.

PREPARATION 5

3-Pyridylcarbonyl)-2-oxindole

To a solution of 2.1 g (0.090 mole) of sodium metal in 100 ml of ethanol, was added 10.0 g (0.075 mole) of 2-oxindole, followed by 13.6 g (0.090 mole) of ethyl nicotinate. The resulting slurry was heated under reflux for 3 hours and then the mixture was cooled and filtered. The residue was discarded, and the filtrate was evaporated in vacuo. The residue thus obtained was dissolved in ca. 150 ml of water, and the aqueous solution was washed with chloroform. To the aqueous solution was then added 5.8 ml of glacial acetic acid and the resulting mixture was cooled in an ice-bath. The solid was recovered by filtration and recrystallized from ethanol to give 3.3 g of the title compound as yellow needles, m.p. 169°–170° C.

Analysis: Calcd. for $C_{14}H_{10}N_2O_2$: C, 70.58; H, 4.23; N, 11.76%. Found: C, 70.66; H, 4.41; N, 11.73%.

In like manner, 3-(2-pyrrolylcarbonyl)-2-oxindole can be prepared by reaction of 2-oxindole with sodium ethoxide and ethyl pyrrole-2-carboxylate in ethanol.

PREPARATION 6

By reacting the appropriate 2-oxindole with the requisite acid chloride of the formula $R^1$-CO-Cl, using the procedure of Preparation 1, the following compounds can be prepared.

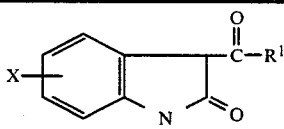

| X | $R^1$ |
|---|---|
| H | isobutyl |
| H | cycloheptyl |
| H | 3-phenylpropyl |
| H | phenyl |
| 5-F | 2-furyl |
| 5-F | cyclopentyl |
| 5-F | 3-furyl |
| 6-F | (3-thienyl)methyl |
| 6-F | (2-furyl)methyl |
| 5-Cl | (2-thienyl)methyl |
| 6-Cl | 2-furyl |
| 5-Br | (3-furyl)methyl |
| 6-Br | n-hexyl |
| 5-$CF_3$ | n-butyl |
| 6-$CF_3$ | 3-thienyl |
| 6-$CF_3$ | cyclopropyl |
| 6-$CF_3$ | ethyl |
| 6-$CF_3$ | 1-phenylethyl |

PREPARATION 7

5-Chloro-2-oxindole

To a stirred slurry of 100 g (0.55 mol) of 5-chloroisatin in 930 ml of ethanol was added 40 ml (0.826 mol) of hydrazine hydrate, resulting in a red solution. The solution was heated under reflux for 3.5 hours, during which time a precipitate appeared. The reaction mixture was stirred overnight, and then the precipitate was recovered by filtration to give 5-chloro-3-hydrazono-2-oxindole as a yellow solid, which was dried in a vacuum oven. The dried solid weighed 105.4 g.

The dried solid was then added portionwise, during 10 minutes, to a solution of 125.1 g of sodium methoxide in 900 ml of absolute ethanol. The resultant solution was heated under reflux for 10 minutes and then it was concentrated in vacuo to a gummy solid. The gummy solid was dissolved in 400 ml of water and the aqueous solution thus obtained was decolorized with activated carbon and then poured into a mixture of 1 liter of water and 180 ml of concentrated hydrochloric acid containing ice chips. A tan solid precipitated and it was collected by filtration and washed thoroughly with water. The solid was dried and then it was washed with diethyl ether. Finally it was recrystallized from ethanol to give 48.9 g of the title compound, m.p. 193°–195° C. (dec).

In an analogous fashion, 5-methylisatin was converted into 5-methyl-2-oxindole by treatment with hydrazine hydrate followed sodium ethoxide in ethanol. The product melted at 173°–174° C.

PREPARATION 8

4,5-Dimethyl-2-oxindole and 5,6-dimethyl-2-oxindole 3,4-Dimethylaniline was converted into 3,4-dimethylisonitrosoacetanilide by reaction with chloral hydrate and hydroxylamine, using the method described in "Organic Syntheses," Collective Volume 1, page 327. The 3,4-dimethyl-isonitrosoacetanilide was cyclized with sulfuric acid, according to the method of Baker et al., Journal of Organic Chemistry, 17, 149 (1952), to give 4,5-dimethylisatin (m.p. 225°–226° C.) and 5,6-dimethylisatin (m.p. 217°–218° C.).

4,5-Dimethylisatin was converted into 4,5-dimethyl-2-oxindole, m.p. 245.5°–247.5° C., by treatment with hydrazine hydrate, followed by sodium ethoxide in ethanol, substantially according to the procedure of Preparation 7.

In like manner, 5,6-dimethylisatin was converted into 5,6-dimethyl-2-oxindole, m.p. 196.5°–198° C., by treatment with hydrazine hydrate, followed by sodium ethoxide in ethanol, substantially according to the procedure of Preparation 7.

PREPARATION 9

4-Chloro-2-oxindole and 6-chloro-2-oxindole

A. 3-Chloro-isonitrosoacetanilide

To a stirred solution of 113.23 g (0.686 mol) of chloral hydrate in 2 liters of water was added 419 g (2.95 mol) of sodium sulfate, followed by a solution prepared from 89.25 g (0.70 mol) of 3-chloroaniline, 62 ml of concentrated hydrochloric acid and 500 ml of water. A thick precipitate formed. To the reaction mixture was then added, with stirring, a solution of 155 g (2.23 mol) of hydroxylamine in 500 ml of water. Stirring was continued and the reaction mixture was warmed slowly and it was maintained between 60° and 75° C. for approximately 6 hours, during which time an additional 1 liter of water had been added to facilitate stirring. The reaction mixture was then cooled and the precipitate was recovered by filtration. The wet solid was dried to give 136.1 g of 3-chloro-isonitrosoacetanilide.

B. 4-Chloroisatin and 6-chloroisatin

To 775 ml of concentrated sulfuric acid, preheated to 70° C., was added, with stirring, 136 g of 3-chloro-isonitrosoacetanilide at such a rate as to maintain the reaction medium at a temperature between 75° and 85° C. When all the solid had been added, the reaction mixture was heated at 90° C. for an additional 30 minutes. The reaction mixture was then cooled, and poured slowly onto ca. 2 liters of ice, with stirring. Additional ice was added as necessary to maintain the temperature below room temperature. A red-orange precipitate formed which was recovered by filtration, washed with water and dried. The resultant solid was slurried in 2 liters of water, and then it was brought into solution by the addition of ca. 700 ml of 3N sodium hydroxide. The solution was filtered, and then pH was adjusted to 8 with concentrated hydrochloric acid. At this point, 120 ml of a mixture of 80 parts water and 20 parts concentrated hydrochloric acid was added. The solid which precipitated was recovered by filtration, washed with water and dried to give 50 g of crude 4-chloroisatin. The filtrate from which the 4-chloroisatin had been recovered was further acidified to pH 0 using concentrated hydrochloric acid, whereupon a further precipitate formed. It was recovered by filtration, washed with water and dried, to give 43 g of crude 6-chloroisatin.

The crude 4-chloroisatin was recrystallized from acetic acid to give 43.3 g of material melting at 258°–259° C.

The crude 6-chloroisatin was recrystallized from acetic acid to give 36.2 g of material melting at 261°–262° C.

C. 4-Chloro-2-oxindole

To a stirred slurry of 43.3 g of 4-chloroisatin in 350 ml of ethanol was added 17.3 ml of hydrazine hydrate, and then the reaction mixture was heated under reflux for 2 hours. The reaction mixture was cooled, and the precipitate was recovered by filtration to give 43.5 g of 4-chloro-3-hydrazono-2-oxindole, m.p. 235°–236° C.

To a stirred solution of 22 g of sodium in 450 ml of anhydrous ethanol was added, portionwise, 43.5 g of 4-chloro-3-hydrazono-2-oxindole, and the resulting solution was heated under reflux for 30 minutes.

The cooled solution was then concentrated to a gum, which was dissolved in 400 ml of water and decolorized using activated carbon. The resulting solution was poured onto a mixture of 1 liter of water and 45 ml of concentrated hydrochloric acid. The precipitate which formed was recovered by filtration, dried and recrystallized from ethanol, giving 22.4 g of 4-chloro-2-oxindole, m.p. 216°–218° C. (dec).

D. 6-Chloro-2-oxindole

Reaction of 36.2 g of 6-chloroisatin with hydrazine hydrate followed by sodium ethoxide in ethanol, substantially according to C above, afforded 14.2 g of 6-chloro-2-oxindole, m.p. 196°–198° C.

PREPARATION 10

5,6-Difluoro-2-oxindole

Reaction of 3,4-difluoroaniline with chloral hydrate and hydroxylamine followed cyclization with sulfuric acid, in a manner analogous to Parts A and B of Preparation 9, gave 5,6-difluoroisatin, which was reacted with hydrazine hydrate followed by sodium methoxide in ethanol, in a manner analogous to Preparation 7, to give the title compound, m.p. 187°–190° C.

PREPARATION 11

5-Fluoro-2-oxindole

To a stirred solution of 11.1 g (0.1 mol) of 4-fluoroaniline in 200 ml of dichloromethane, at −60° to −65° C., was added, dropwise, a solution of 10.8 g (0.1 mol) of t-butyl hypochlorite in 25 ml of dichloromethane. Stirring was continued for 10 minutes at −60° to −65° C., and then was added, dropwise, a solution of 13.4 g (0.1 mol) of ethyl 2-(methylthio)acetate in 25 ml of dichloromethane. Stirring was continued at −60° C. for 1 hour and then was added, dropwise, at −60° to −65° C., a solution of 11.1 g (0.11 mol) of triethylamine in 25 ml of dichloromethane. The cooling bath was removed, and when the reaction mixture had warmed to room temperature, 100 ml of water was added. The phases were separated, and the organic phase was washed with saturated sodium chloride solution, dried ($Na_2SO_4$) and evaporated in vacuo. The residue was dissolved in 350 ml of diethyl ether, to which was added 40 ml of 2N hydrochloric acid. This mixture was stirred at room temperature overnight. The phases were separated and the ether phase was washed with water, followed saturated sodium chloride. The dried ($Na_2SO_4$) ether phase was evaporated in vacuo to give 17 g of an orange-brown solid which was triturated under isopropyl ether. The solid was then recrystallized form ethanol, to give 5.58 g of 5-fluoro-3-methylthio-2-oxindole, m.p. 151.5°–152.5° C.

Analysis: Calcd. for $C_9H_8ONFS$: C, 54.80; H, 4.09; N, 7.10%. Found: C, 54.74; H, 4.11; N, 7.11%.

A sample of the above 5-fluoro-3-methylthio-2oxindole (986 mg, 5.0 mmol) was added to 2 teaspoonsful of Raney nickel under 50 ml of absolute ethanol, and then the reaction mixture was heated under reflux for 2 hours. The catalyst was removed by decantation and was washed with absolute ethanol. The combined ethanol solutions were evaporated in vacuo and the residue was dissolved in dichloromethane. The dichloromethane solution was dried ($Na_2SO_4$) and evaporated in vacuo to give 475 mg of 5-fluoro-2-oxindole, m.p. 121°–134° C.

In analogous fashion, 4-trifluoromethylaniline was reacted with t-butyl hypochlorite, ethyl 2-(methylthio)acetate and triethylamine followed by reduction of the 3-thiomethyl-5-trifluoromethyl-2-oxindole thus obtained with Raney nickel, to give 5-trifluoromethyl-2-oxindole, m.p. 189.5°–190.5° C.

PREPARATION 12

5-Methoxy-2-oxindole

5-Methoxy-2-oxindole was prepared from 4-methoxyaniline in a manner similar to the procedure of Preparation 11, except that the initial chlorination step was carried out using a solution of chlorine gas in dichloromethane in place of t-butyl hypochlorite. The title product melted at 150.5°–151.5° C.

PREPARATION 13

6-Chloro-5-fluoro-2-oxindole

To 130 ml of toluene was added, with stirring, 24.0 g (0.165 mole) of 3-chloro-4-fluoroaniline and 13.5 ml (0.166 mole) of pyridine. The resulting solution was cooled to ca. 0° C. and 13.2 ml (0.166 mole) of 2-chloroacetyl chloride was added. The reaction mixture was stirred at room temperature for 5 hours and then it was extracted twice with 100 ml of 1N hydrochloric acid, followed by 100 ml of saturated sodium chloride solution. The resulting toluene solution was dried using magnesium sulfate, and then it was concentrated in vacuo to give 32.6 g (88% yield) of N-(2-chloroacetyl)-3-chloro-4-fluoroaniline.

A 26.63-g sample of the N-(2-chloroacetyl)-3-chloro-4-fluoroaniline was thoroughly mixed with 64 g of anhydrous aluminum chloride, and the mixture was heated at 210°–230° C. for 8.5 hours. The reaction mixture was then poured onto a mixture of ice and 1N hydrochloric acid, with stirring. Stirring was continued for 30 minutes, and then the solid was collected by filtration (22.0 g). The solid was dissolved in 1:1 ethyl acetate-hexane and chromatographed on 800 g of silica gel. Elution of the column, followed by evaporation of the fractions, produced 11.7 g of the N-(2-chloroacetyl)-3-chloro-4-fluoroaniline, followed by 3.0 g of 6-chloro-5-fluoro-2-oxindole. The latter material was recrystallized from toluene to give 1.70 g (7% yield) of the title compound, m.p. 196°-206° C. Analysis by NMR spectroscopy indicated that the product was contaminated by some 4-chloro-5-fluoro-2-oxindole.

PREPARATION 14

6-Fluoro-5-methyl-2-oxindole

An intimate mixture of 11.62 g (57.6 mmol) of N-(2-chloroacetyl)-3-fluoro-4-methylaniline and 30.6 g (229.5 mmol) of anhydrous aluminum chloride was heated to 210°-220° C. After 4 hours, the reaction mixture was cooled and then added to 100 ml of 1N hydrochloric acid and 50 ml of ice. A tan solid formed, which was collected by filtration and recrystallized from aqueous ethanol. Three crops were obtained, weighing 4.49 g, 2.28 g and 1.0 g, respectively. The crop weighing 1.0 g was further recrystallized from water to give 280 mg of the title compound, m.p. 168.5°-171° C.

PREPARATION 15

6-Bromo-2-oxindole

To 9.4 g of sodium hydride was added 195 ml of dimethyl sulfoxide, followed by the dropwise addition of 22.37 ml of dimethyl malonate. At the end of the addition, the mixture was heated to 100° C. and maintained at that temperature for 40 minutes. At this point, 25 g of 1,4-dibromo-2-nitrobenzene was added all at once. The reaction mixture was maintained at 100° C. for 4 hours and then it was added to 1.0 liter of saturated ammonium chloride solution. The resulting mixture was extracted with ethyl acetate and the extracts were washed with ammonium chloride solution, water and saturated sodium chloride. The dried (MgSO$_4$) solvent was evaporated, and the residue was recrystallized from ethyl acetate-hexane to give 22.45 g of dimethyl 2-(4-bromo-2-nitrophenyl)malonate.

A solution of 17.4 g of dimethyl 2-(4-bromo-2-nitrophenyl)malonate and 4.6 g of lithium chloride in 150 ml of dimethyl sulfoxide was placed in an oil bath at 100° C. After 3 hours, the reaction mixture was cooled to room temperature and then it was poured into a mixture of 500 ml of ethyl acetate and 500 ml of saturated sodium chloride solution. The layers were separated and the aqueous layer was extracted with further ethyl acetate. The combined organic layers were washed with saturated sodium chloride solution, dried using sodium sulfate, and then evaporated in vacuo. The residue was chromatographed using silica gel as adsorbant and ethyl acetate-hexane mixture as eluant. This afforded 9.4 g of methyl 2-(4-bromo-2-nitrophenyl)acetate.

To a solution of 7.4 g of methyl 2-(4-bromo-2-nitrophenyl)acetate in 75 ml of acetic acid was added 6.1 g of iron powder. The reaction mixture was placed in an oil bath at 100° C. After 1 hour, the solvent was removed by evaporation in vacuo, and the residue was dissolved in 250 ml of ethyl acetate. The solution was filtered, washed with saturated sodium chloride solution, dried using sodium sulfate, decolorized using activated carbon, and evaporated in vacuo. This afforded 5.3 g of 6-bromo-2-oxindole as a white crystalline solid, m.p. 213°-214° C.

In like manner, starting with 1,4,5-trichloro-2-nitrobenzene, 5,6-dichloro-2-oxindole was prepared, m.p. 209°-210° C.

PREPARATION 16

6-Phenyl-2-oxindole

To 3.46 g. (0.072 mole) of sodium hydride was added 50 ml. of dimethyl sulfoxide followed by the dropwise addition of a solution of 8.2 ml. (0.072 mole) of dimethyl malonate in 10 ml. of dimethyl sulfoxide, with stirring. After completion of the addition, stirring was continued for 1 hour, and then a solution of 10 g. (0.036 mole) of 4-bromo-3-nitro-diphenyl in 50 ml. of dimethyl sulfoxide was added. The reaction mixture was heated to 100° C. for 1 hour, cooled, and poured onto a mixture of ice-water containing 5 g. of ammonium chloride. The mixture thus obtained was extracted with ethyl acetate, and the extracts were washed with sodium chloride solution and dried using magnesium sulfate. Evaporation in vacuo to give an oil, which was chromatographed using silica gel and then recrystallized from methanol to afford 6 g. of dimethyl 2-(3-nitro-4-diphenylyl)malonate, m.p. 82°-83° C.

A portion (5 g.) of the above nitro compound was reduced with hydrogen over a platinum catalyst, in a mixture of 50 ml. of tetrahydrofuran and 10 ml. of methanol, at a pressure of ca 5 kg/cm$^2$, to give the corresponding amine. The latter compound was refluxed in ethanol for 16 hours, and then the product was recovered by solvent evaporation and recrystallized from methanol to give 1.1 g. of ethyl 6-phenyl-2-oxindole-1-carboxylate, m.p. 115°-117° C.

The above ethyl ester (1.0 g.) and 100 ml. of 6N hydrochloric acid was heated under reflux for 3 hours and then allowed to stand at room temperature for 3 days. The solid was collected by filtration and dried, to give 700 mg. of 6-phenyl-2-oxindole, m.p. 175°-176° C.

PREPARATION 17

5-Acetyl-2-oxindole

To 95 ml. of carbon disulfide was added 27 g. (0.202 mole) of aluminum chloride, followed by the dropwise addition of a solution of 3 ml. (0.042 mole) of acetyl chloride in 5 ml. of carbon disulfide, with stirring. Stirring was continued for 5 minutes and then 4.4 g. (0.033 mole) of 2-oxindole was added. The resulting mixture was heated under reflux for 4 hours and cooled. The carbon disulfide was removed by decantation and the residue was triturated under water and recovered by filtration. After drying, 3.2 g. of the title compound was obtained, m.p. 225°-227° C.

Reaction of 2-oxindole with benzoyl chloride and with 2-thenoyl chloride in the presence of aluminum chloride, substantially according to the above procedure, afforded the following compounds:

5-benzoyl-2-oxindole, m.p. 203°-205° C. (from CH$_3$OH) and 5-(2-thenoyl)-2-oxindole, m.p. 211°-213° C. (from CH$_3$CN).

PREPARATION 18

5-Bromo-2-oxindole can be prepared by bromination of 2-oxindole; see further Beckett et al., *Tetrahedron*, 24, 6093 (1968) and Sumpter et al., *Journal of the American Chemical Society*, 67, 1656 (1945).

5-n-Butyl-2-oxindole can be prepared by reaction of 5-n-butylisatin with hydrazine hydrate followed by sodium methoxide in ethanol, according to the procedure of Preparation 7. 5-n-Butylisatin can be prepared from 4-n-butylaniline by treatment with chloral hydrate and hydroxylamine, followed by cyclization with sulfuric acid, according to the procedure of Parts A and B of Preparation 9.

5-Ethoxy-2-oxindole can be prepared by conversion of 3-hydroxy-6-nitro-toluene into 3-ethoxy-6-nitrotoluene by standard methods (potassium carbonate and ethyl iodide in acetone), followed by conversion of the 3-ethoxy-6-nitrotoluene into 5-ethoxy-2-oxindole by the method described by Beckett et al., *Tetrahedron*, 24, 6093 (1968), for the conversion of 3-methoxy-6-nitrotoluene into 5-methoxy-2-oxindole. 5-n-Butoxy-2-oxindole can be prepared in like manner, but substituting n-butyl iodide for ethyl iodide.

5,6-Dimethoxy-2-oxindole can be prepared by the method of Walker, *Journal of the American Chemical Society*, 77, 3844 (1955).

7-Chloro-2-oxindole can be prepared by the method described in U.S. Pat. No. 3,882,236.

4-Thiomethyl-2-oxindole and 6-thiomethyl-2-oxindole can be prepared by the method described in U.S. Pat. No. 4,006,161. 5-n-Butylthio-2-oxindole can be prepared in like manner, but substituting 4-butylthioaniline for the 3-methylthioaniline.

6-Fluoro-2-oxindole can be prepared according to Protiva et al., *Collection of Czechoslovakian Chemical Communications*, 44, 2108 (1979) and U.S. Pat. No. 4,160,032.

6-Trifluoromethyl-2-oxindole can be prepared according to Simet, *Journal of Organic Chemistry*, 28, 3580 (1963).

6-Methoxy-2-oxindole can be prepared according to Wieland et al., *Chemische Berichte*, 96, 253 (1963).

5-Nitro-2-oxindole can be prepared by the method of Sumpter et al., *Journal of the American Chemical Society*, 67, 499 (1945).

5-Cyclopropyl-2-oxindole and 5-cycloheptyl-2-oxindole can be prepared by reaction of 5-cyclopropylisatin and 5-cycloheptylisatin, respectively, with hydrazine hydrate followed by sodium methoxide in ethanol, according to the procedure of Preparation 7. 5-Cyclopropylisatin and 5-cycloheptylisatin can be prepared from 4-cyclopropylaniline and 4-cycloheptylaniline, respectively, by treatment with chloral hydrate and hydroxylamine, followed by cyclization with sulfuric acid, according to Parts A and B of Preparation 9.

I claim:

1. A 1,3-diacyl-2-oxindole compound of the formula:

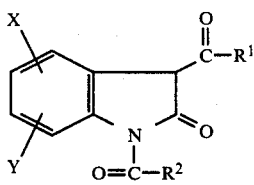

and the pharmaceutically-acceptable base salts thereof; wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

$R^1$ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)alkyl having 1 to 3 carbons in said alkyl and naphthyl;

wherein the substituent on said substituted phenyl, said (substituted phenyl)alkyl and said (substituted phenoxy)alkyl is selected from the group consisting of fluoro, bromo, chloro, alkyl having 1 to 4 carbons, alkoxy having 1 to 4 carbons and trifluoromethyl;

and $R^2$ is alkyl having from 1 to 5 carbons.

2. A compound according to claim 1, wherein
X is at the 5-position or the 6-position and it is selected from the group consisting of hydrogen, fluoro, chloro, bromo and trifluoromethyl; and Y is hydrogen;

and $R^1$ is selected from the group consisting of alkyl having from 1 to 6 carbons, cycloalkyl having from 3 to 7 carbons, phenyl and phenylalkyl having 1 to 3 carbons in said alkyl.

3. A method of eliciting an analgesic response in a mammalian subject, which comprises administering to said mammalian subject an analgesic response eliciting amount of a 1,3-diacyl-2-oxindole compound of the formula

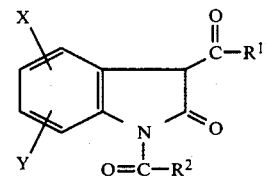

or a pharmaceutically-acceptable base salt thereof; wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

$R^1$ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)alkyl having 1 to 3 carbons in said alkyl and naphthyl;

wherein the substituent on said substituted phenyl, said (substituted phenyl)alkyl and said (substituted phenoxy)alkyl is selected from the group consisting of fluoro, chloro, bromo, alkyl having 1 to 4 carbons, alkoxy having 1 to 4 carbons and trifluoromethyl;

and $R^2$ is alkyl having from 1 to 5 carbons.

4. The method according to claim 3, wherein

X is at the 5-position or the 6-position and it is selected from the group consisting of hydrogen, fluoro, chloro, bromo and trifluoromethyl; and Y is hydrogen;

and $R^1$ is selected from the group consisting of alkyl having from 1 to 6 carbons, cycloalkyl having from 3 to 7 carbons, phenyl and phenylalkyl having 1 to 3 carbons in said alkyl.

5. A method of treating an inflammatory disease in a mammalian subject, which comprises administering to said mammalian subject an inflammatory disease treating amount of a 1,3-diacyl-2-oxindole compound of the formula

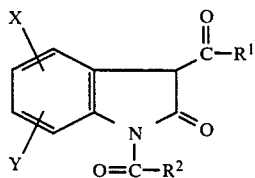

or a pharmaceutically-acceptable base salt thereof, wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

$R^1$ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)alkyl having 1 to 3 carbons in said alkyl and naphthyl;

wherein the substituent on said substituted phenyl, said (substituted phenyl)alkyl and said (substituted phenoxy)alkyl is selected from the group consisting of fluoro, chloro, bromo, alkyl having 1 to 4 carbons, alkoxy having 1 to 4 carbons and trifluoromethyl;

and $R^2$ is alkyl having from 1 to 5 carbons.

6. The method according to claim 5 wherein

X is at the 5-position or the 6-position and it is selected from the group consisting of hydrogen, fluoro, chloro, bromo and trifluoromethyl; and Y is hydrogen;

and $R^1$ is selected from the group consisting of alkyl having from 1 to 6 carbons, cycloalkyl having from 3 to 7 carbons, phenyl and phenylalkyl having 1 to 3 carbons in said alkyl;

7. An analgesic or antiinflammatory pharmaceutical composition, which comprises a pharmaceutically-acceptable carrier and an effective analgesic or antiinflammatory amount of a 1,3-diacyl-2- oxindole compound according to claim 1, and wherein the weight ratio of the pharmaceutically-acceptable carrier to the 1,3-diacyl-2-oxindole compound is in the range from 1:4 to 4:1.

8. A compound of the formula

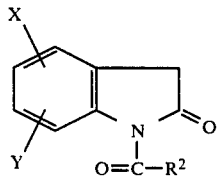

wherein X is selected from the group consisting of hydrogen, 5-fluoro, 5-chloro and 5-trifluoromethyl; Y is selected from the group consisting of hydrogen 6-fluoro, 6-chloro and 6-trifluoromethyl;

and $R^2$ is alkyl having 1 to 5 carbons;

provided that X and Y are not both hydrogen.

9. A compound according to claim 8, wherein $R^2$ is methyl.

10. The compound according to claim 9, wherein X is 5-chloro and Y is hydrogen.

11. A compound according to claim 9, wherein X is 5-fluoro or 5-chloro and Y is 6-fluoro or 6-chloro.

12. The compound according to claim 11, wherein X is 5-fluoro and Y is 6-chloro.

13. The compound according to claim 1, wherein X is 5-chloro, Y is hydrogen, $R^1$ is phenyl and $R^2$ is methyl.

14. The compound according to claim 1, wherein X is 5-chloro, Y is hydrogen, $R^1$ is benzyl and $R^2$ is methyl.

15. The method according to claim 3, wherein X is 5-chloro, Y is hydrogen, $R^1$ is phenyl and $R^2$ is methyl.

16. The method according to claim 3, wherein X is 5-chloro, Y is hydrogen, $R^1$ is benzyl and $R^2$ is methyl.

17. The method according to claim 5, wherein X is 5-chloro, Y is hydrogen, $R^1$ is phenyl and $R^2$ is methyl.

18. The method according to claim 5, wherein X is 5-chloro, Y is hydrogen, $R^1$ is benzyl and $R^2$ is methyl.

* * * * *